United States Patent
Bonomi (10) Patent No.: US 11,179,046 B2
(45) Date of Patent: Nov. 23, 2021

(54) METHOD AND SYSTEM FOR DETECTION OF ATRIAL FIBRILLATION

(71) Applicant: KONINKLIJKE PHILIPS N.V., Eindhoven (NL)

(72) Inventor: Alberto Giovanni Bonomi, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 77 days.

(21) Appl. No.: 16/483,133

(22) PCT Filed: Jan. 30, 2018

(86) PCT No.: PCT/EP2018/052202
§ 371 (c)(1),
(2) Date: Aug. 2, 2019

(87) PCT Pub. No.: WO2018/141710
PCT Pub. Date: Aug. 9, 2018

(65) Prior Publication Data
US 2020/0229708 A1 Jul. 23, 2020

Related U.S. Application Data

(60) Provisional application No. 62/454,226, filed on Feb. 3, 2017.

(51) Int. Cl.
*A61B 5/0205* (2006.01)
*A61B 5/364* (2021.01)
(Continued)

(52) U.S. Cl.
CPC .......... *A61B 5/0205* (2013.01); *A61B 5/0006* (2013.01); *A61B 5/02416* (2013.01);
(Continued)

(58) Field of Classification Search
None
See application file for complete search history.

(56) References Cited

U.S. PATENT DOCUMENTS

2011/0208079 A1 8/2011 Babaeizadeh et al.
2012/0053432 A1 3/2012 Huiku et al.
(Continued)

FOREIGN PATENT DOCUMENTS

GB 2448975 A 11/2008
WO 2015150199 A1 10/2015

OTHER PUBLICATIONS

International Search Report and Written Opinion, International Application No. PCT/EP2018/052202, dated May 7, 2018.
(Continued)

*Primary Examiner* — Brian T Gedeon (57) ABSTRACT

A method (100) for monitoring an individual's (710) cardiac activity, the method including the steps of: (i) obtaining (110), during a calibration phase, ECG data for the individual from a ECG monitor; (ii) obtaining (120), during the calibration phase, cardiac activity data for the individual from a wearable device including a plethysmographic sensor; (iii) obtaining (130), during a monitoring phase, cardiac activity data for the individual from the wearable device including the plethysmographic sensor; (iii) generating (140) calibration data from the ECG data and cardiac activity data obtained during the calibration phase; and (iv) calibrating (150), using the calibration data, the cardiac activity data obtained by the wearable device during the monitoring phase.

20 Claims, 6 Drawing Sheets

(51) Int. Cl.
  *A61B 5/024* (2006.01)
  *A61B 5/00* (2006.01)
  *A61B 5/352* (2021.01)
  *A61B 5/361* (2021.01)

(52) U.S. Cl.
  CPC .......... *A61B 5/02438* (2013.01); *A61B 5/352* (2021.01); *A61B 5/361* (2021.01); *A61B 5/364* (2021.01); *A61B 2560/0223* (2013.01)

(56) References Cited

U.S. PATENT DOCUMENTS

| | | | |
|---|---|---|---|
| 2014/0323894 A1 | 10/2014 | Zhang et al. | |
| 2015/0182132 A1* | 7/2015 | Harris | A61B 5/7282 340/870.01 |
| 2016/0148531 A1* | 5/2016 | Bleich | G09B 19/0038 434/247 |
| 2018/0279888 A1* | 10/2018 | Wang | A61B 5/0205 |

OTHER PUBLICATIONS

Bonomi, A. et al., "Atrial Fibrillation Detection using Photoplethysmography and Acceleration Data at the Wrist", Computing in Cardiology 2016; 43:277-280.

Lemay, M. et al., "Wrist-Located Optical Device for Atrial Fibrillation Screening: A Clinical Study on Twenty Patients", Computing in Cardiology 2016; 43:681-684.

Babaeizadeh, S. et al., "Improvements in atrial fibrillation detection for real-time monitoring", Journal of Electrocardiology, 42 (2009), 522-526.

Suzuki, T. et al., "Development of the Irregular Pulse Detection Method in Daily Life using Wearable Photoplethysmographic Sensor", 31st Annual International Conference of the IEEE EMBS, Minneapolis, Minnesota, USA, Sep. 2-6, 2009.

Moody, G. et al., "A new method for detecting atrial fibrillation using R-R intervals", Massachusetts Institute of Technology, Computers in Cardiology, 1983.

* cited by examiner

METHOD AND SYSTEM FOR DETECTION OF ATRIAL FIBRILLATION

This application is the U.S. National Phase application under 35 U.S.C. § 371 of International Application No. PCT/EP2018/052202, filed on 30 Jan. 2018, which claims the benefit of U.S. Provisional Application Ser. No. 62/454, 226, filed 3 Feb. 2017. These applications are hereby incorporated by reference herein.

TECHNICAL FIELD

The present disclosure is directed generally to methods and systems for monitoring cardiac activity using a combination of an ECG monitor and a wearable device including a plethysmographic sensor.

BACKGROUND

Atrial fibrillation (AF) is a cardiac condition affecting millions of individuals, and is the most common type of arrhythmia. AF is particularly prevalent after the age of 60 and can lead to severe events such as embolic stroke and heart failure. Preventing, detecting, and treating AF is an important goal for individuals and healthcare professionals.

Early detection of AF is problematic because of its paroxysmal nature, meaning that the condition typically appears suddenly and autonomously stops. For this reason, in order to properly capture AF events which are sporadic and short, long term monitoring of cardiac activity is essential especially in the early stages of development. Unfortunately, current AF screening and monitoring technology is based on obtrusive and costly devices such as Holter® monitors or implantable loop recorders. These monitors obtain high quality (multiple-lead ECG) information such that a technician can provide a highly accurate interpretation of the patient heart rhythm. However, this system is obtrusive and as a result the typical monitoring duration is of 24 to 48 hours only. While implantable loop recorders are capable of tracking ECG and the patient heart rhythm for very long time, including up to a few years, they carry high costs and require a surgical procedure.

Emerging digital health and wearable technologies are opening new avenues to allow for user-acceptable and non-stigmatizing long-term cardiac monitoring. A wrist wearable device, like a digital watch, equipped with a photo-plethysmographic (PPG) sensor can be used to unobtrusively track heart rhythm in patients and detect episodes of suspect AF. The disadvantage is that the system may suffer from poor specificity due to the inability to clearly discriminate AF from premature beats and other types of supra-ventricular tachycardia. This accuracy problem may be particularly relevant in elderly subjects in whom the frequency of premature beats throughout a day may be large. Furthermore, some patients may suffer from premature beats especially at night while other patients may show premature beats after some moderate activity or after food intake. Medication intake may also modify the likelihood of premature beats in patients. This patient-specific heterogeneity in the occurrence and density of premature beats can prevent accurate arrhythmia detection by a PPG-based monitor or sensor.

SUMMARY

In View of the foregoing, it would be beneficial to provide methods and systems that detect atrial fibrillation using a scheduled combination of an ECG monitor and a wearable device including a photo-plethysmographic sensor.

Accordingly, the present disclosure is directed to methods and systems for monitoring cardiac activity using wearable devices. Various embodiments and implementations herein are directed to a device or system that receives information about an individual's cardiac activity, including heart rhythm, heart rate, and other activity, from a combination of a wearable ECG monitor and a wearable device including a plethysmographic sensor. The individual utilizes ECG monitoring technology, such as a wearable Holter device, to obtain ECG data for a short initial period, such as up to 1 or 2 days, although longer or shorter times are possible. During that same initial time period, the individual utilizes a wearable photo-plethysmographic (PPG) sensor to obtain data about cardiac activity. Cardiac activity can be defined, for example, as the rhythm and rate of the pulsatile pattern of the circulating blood due to cardiac contraction as measured by the plethysmographic sensor, although other types of cardiac activity might be analyzed by the systems and methods described herein. The system performs an individual-specific calibration of cardiac activity, and applies that calibration to data received from just the wearable photo-plethysmographic (PPG) sensor during the subsequent monitoring period.

Generally in one aspect, a method for monitoring an individual's cardiac activity is provided. The method includes the steps of: (i) obtaining, during a calibration phase, ECG data for the individual from a ECG monitor; (ii) obtaining, during the calibration phase, cardiac activity data for the individual from a wearable device including a plethysmographic sensor; (iii) obtaining, during a monitoring phase, cardiac activity data for the individual from the wearable device including the plethysmographic sensor; (iv) generating calibration data from the ECG data and cardiac activity data obtained during the calibration phase; and (v) calibrating, using the calibration data, the cardiac activity data obtained by the wearable device during the monitoring phase.

According to an embodiment, the method further includes the step of communicating the calibrated cardiac activity data to the individual or another recipient.

According to an embodiment, the ECG monitor is worn by the individual.

According to an embodiment, the plethysmographic sensor is a photo-plethysmographic sensor.

According to an embodiment, the calibration data includes a personalized cardiac activity threshold.

According to an embodiment, the calibrating step includes a comparison of the cardiac activity data obtained by the wearable device during the monitoring phase to the personalized cardiac activity threshold.

According to an embodiments, generating the calibration data includes: identifying at least one cardiac event from the ECG data, and generating the personalized threshold based on the cardiac activity data excluding at least one portion of the calibration cardiac activity data corresponding to the at least one cardiac event identified in the ECG data.

According to an embodiment, the calibration phase and the monitoring phase are not overlapping.

According to an embodiment, the ECG data is obtained during a first calibration phase and the cardiac activity data is obtained during a second calibration phase.

According to an embodiment, the ECG data, calibration cardiac activity, and monitoring cardiac activity each include respective series of R-R irregularity indices.

According to an embodiment, obtaining the ECG data includes: receiving R-R interval data from the ECG monitor; and computing a series R-R irregularity indices from the R-R interval data, wherein the ECG data includes the R-R irregularity indices.

According to an aspect is a system for monitoring an individual's cardiac activity. The system includes: an ECG monitor configured to collect ECG data for the individual during a calibration phase; a wearable device including a plethysmographic sensor and configured to collect, via the plethysmographic sensor, cardiac activity data for the individual during the calibration time period and during a monitoring time period; and a processor configured to: (i) generate calibration data from the ECG data and cardiac activity data obtained during the monitoring phase; and (ii) calibrate, using the calibration data, the cardiac activity data obtained by the wearable device during the monitoring phase.

According to an aspect is a device for analyzing an individual's cardiac activity. The device includes a processor configured to execute the steps of: (i) receiving ECG data obtained by an ECG monitor for an individual during a calibration time period; (iii) receiving cardiac activity data for the individual obtained during the calibration time period by a wearable device including a plethysmographic sensor; (iv) generating calibration data from the ECG data and cardiac activity data obtained during the calibration phase; and (v) calibrating, using the calibration data, the cardiac activity data obtained by the wearable device during the monitoring phase.

As used herein for purposes of the present disclosure, the term "processor" is used generally to describe various apparatus components relating to the operation of the recommendation apparatus, system, or method. A processor can be implemented in numerous ways (e.g., such as with dedicated hardware) to perform various functions discussed herein. A "processor" can employ one or more microprocessors that may be programmed using software (e.g., microcode) to perform various functions discussed herein. A processor may also be implemented as a combination of dedicated hardware to perform some functions. Examples of processor components that may be employed in various embodiments of the present disclosure include, but are not limited to, conventional microprocessors, application specific integrated circuits (ASICs), and field-programmable gate arrays (FPGAs).

In various implementations, a processor may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects discussed herein. The terms "program" or "computer program" are used herein in a generic sense to refer to any type of computer code (e.g., software or microcode) that can be employed to program one or more processors or controllers. As used herein, the term "non-transitory machine-readable medium" will be understood to encompass both volatile and non-volatile memories, but to exclude transitory signals.

The term "user interface" as used herein refers to an interface between a human user or operator and one or more devices that enables communication between the user and the device(s). Examples of user interfaces that may be employed in various implementations of the present disclosure include, but are not limited to, switches, potentiometers, buttons, dials, sliders, track balls, display screens, various types of graphical user interfaces (GUIs), touch screens, microphones and other types of sensors that may receive some form of human-generated stimulus and generate a signal in response thereto.

Various embodiments may further include non-transitory computer-readable storage media, having embodied thereon a firewall program executable by a processor to perform methods described herein.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating various principles.

DETAILED DESCRIPTION OF EMBODIMENTS

The present disclosure describes various embodiments of a method and system for monitoring cardiac activity using wearable devices. More generally, Applicant has recognized and appreciated that it would be beneficial to provide a method or system for long-term unobtrusive monitoring of cardiac activity. A particular goal of utilization of certain embodiments of the present disclosure is to provide a system that gathers and analyzes an individual's cardiac activity and provides the data for a healthcare professional.

In view of the foregoing, various embodiments and implementations are directed to a method and system that obtains cardiac activity data using a scheduled combination of an ECG monitor and a wearable device including a photo-plethysmographic sensor. An individual being monitored wears both the ECG monitor and the photo-plethysmographic sensor during an initial, short calibration period. The individual then wears only the photo-plethysmographic sensor, which is in some embodiments unobtrusive, during a subsequent, longer monitoring period. Using the information obtained during the calibration period, the system performs an individual-specific calibration of cardiac activity, and applies that calibration to data received from the wearable photo-plethysmographic (PPG) sensor during the subsequent monitoring period. Based on the calibration using the ECG data, the data generated by the PPG sensor during the monitoring period is generally more accurate and informative.

Figure 1:
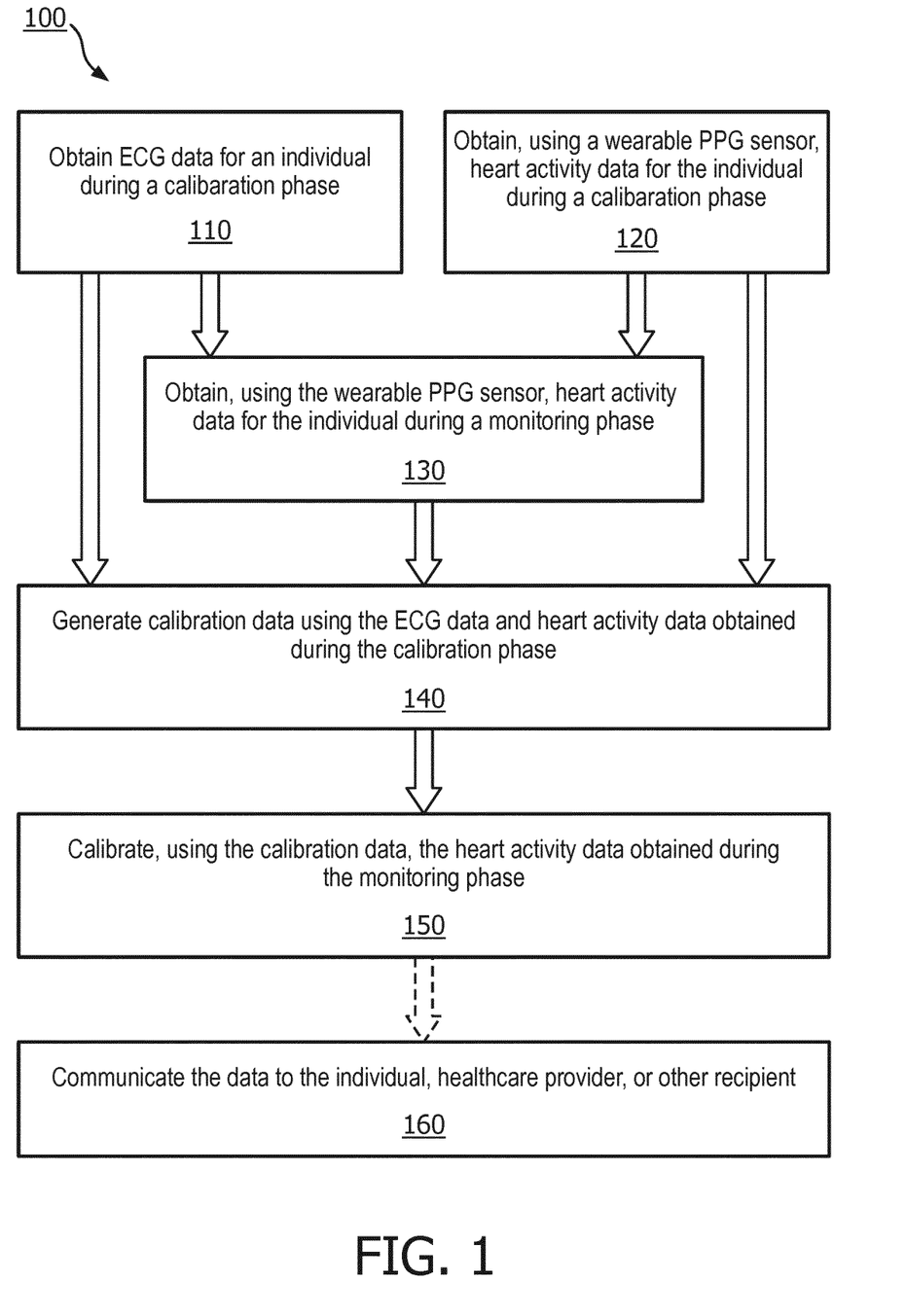
FIG. 1 is a flowchart of a method for monitoring an individual's cardiac activity, in accordance with an embodiment.

Referring to FIG. 1, in one embodiment, is a method 100 for monitoring cardiac activity using a combination of an ECG monitor and a wearable device including a photo-plethysmographic sensor. The cardiac activity data may be heart rate, heart rhythm, heart rate variability (HRV), maximum heart rate, minimum heart rate, RR irregularity index, blood pressure, or any other measurement of cardiac activity.

At step 110 of the method, the individual wears an ECG monitor and obtains ECG data during a calibration phase or time period. According to an embodiment, the ECG monitor is a wearable ECG monitor such as a Holter monitor. The monitor can be, for example, a multi-lead ECG monitor. ECG monitors are commonly utilized by healthcare professionals to diagnose cardiac arrhythmias. During the calibration phase, the ECG monitor is configured or designed to gather clinical information about the user's cardiac activity, including but not limited to normal sinus rhythm, the number and occurrence of arrhythmic events including premature atrial contraction, premature ventricular contraction, atrial fibrillation, tachycardia or bradycardia, and atrial flutter, among many others. The ECG monitor can also be configured or designed to gather clinical information about the user's RR-intervals independently from and/or coupled to each identified heart rhythm type. According to an embodiment, the calibration phase or time period for the ECG monitor is one to two days, such as 12, 24, or 48 hours. However, longer and shorter periods are possible.

At step 120 of the method, which is performed simultaneously with step 110 of the method, the individual wears a wearable device including a plethysmographic sensor such as a photo-plethysmographic sensor (PPG), and obtains cardiac activity data during the calibration phase or time period. According to an embodiment, the wearable device is any wearable device including or capable of including a plethysmographic sensor. For example, the wearable device may be a wearable tracker worn on the wrist, around the neck, or elsewhere on or around the user's body. Typically, the wearable device will have constant or periodic access to the wearer's skin in order to obtain sensor data. However, the plethysmographic sensor may be capable of obtaining data without direct access to the wearer's skin. According to an embodiment, the plethysmographic sensor obtains heart rate data, blood pressure data, respiration data, and/or other types of data.

At step 130 of the method, the individual wears a wearable device including the plethysmographic sensor and obtains cardiac activity data during a monitoring phase or time period. According to an embodiment, the monitoring phase may be before and/or after the calibration phase. The wearable device may be the same wearable device worn by the user during the calibration phase, but the user may switch to a different wearable device for all or part of the monitoring phase. According to an embodiment, the plethysmographic sensor of the wearable device obtains heart rate data, blood pressure data, respiration data, and/or other types of data.

At step 140 of the method, the system generates calibration data using the ECG data and cardiac activity data obtained during the calibration phase of the method. According to an embodiment, this calibration data represents an integration of the ECG data, which provides an RR interval and the associated heart rhythm, and the plethysmographic sensor data. According to an embodiment, the calibration data includes one or more personalized thresholds for cardiac activity data that can then be applied to cardiac activity data obtained by the wearable device during the monitoring phase. The calibration data normalizes the data obtained from the plethysmographic sensor of the wearable device which can vary considerably from user to user and device to device.

According to an embodiment, integration of the ECG data and the plethysmographic sensor data can be an automated process. For example, an algorithm can integrate the data and generate the calibration data including one or more thresholds. According to an embodiment, a healthcare professional can optionally provide or facilitate the provision of the ECG data and the plethysmographic sensor data to the algorithm, including but not limited to identification of one or more AF periods. The identified one or more AF periods can then be excluded from an irregularity analysis, thereby personalizing the AF irregularity threshold. For example, the ECG data may be used to identify AF episodes during the monitoring period. Then, the PPG data that was captured during the same time window where any identified AF episodes occurred may be removed from the PPG data set or otherwise excluded from the following anaylsis. The remaining PPG data may then be used to determine the personalized threshold to be applied during monitoring. For example, the personalized threshold may be set at a percentile (e.g., 2.5%) of the remaining (non-AF event) RR irregularity indices observed in the PPG data. Then, during the monitoring phase, if the monitored RR irregularity index falls below the this personalized threshold (or falls below the threshold for a period of time), an alarm may be raise or AF event may be identified.

Figure 2:
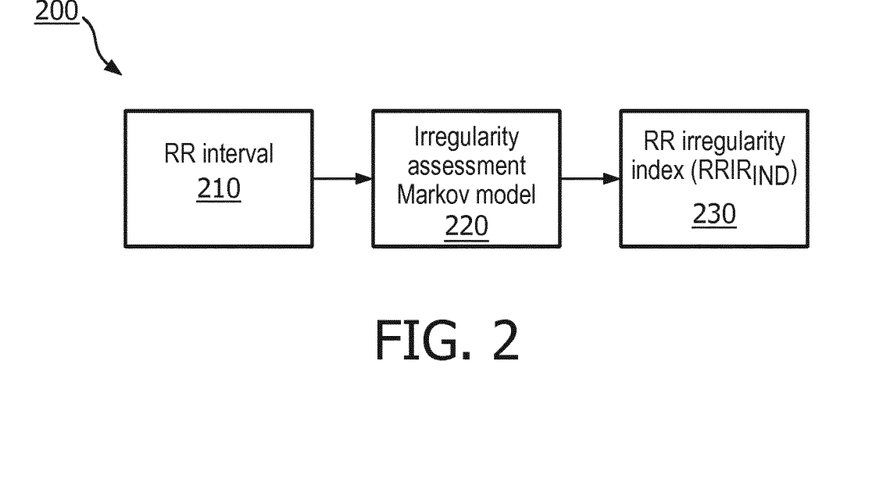
FIG. 2 is a schematic representation of a Markov model system utilized to analyze data obtained from ECG monitoring of a healthy patient, in accordance with an embodiment.

According to an embodiment, RR-intervals and corresponding heart rhythm classifications obtained by the ECG monitor during the calibration phase is processed to determine a level of irregularity in the RR sequence. The level of irregularity can be determined according to a RR-irregularity index ($RRIR_{IND}$). A possible representation of such index is the output of a first-order Markov model. Referring to FIG. 2, in one embodiment, is a schematic representation 200 of a Markov model system which can be utilized to analyze data obtained from ECG monitoring of a healthy patient. Model 200 accepts RR interval data 210 obtained by the ECG monitor, and applies an irregularity assessment Markov model 220 to generate the RR-irregularity index ($RRIR_{IND}$) 230.

Figure 3:
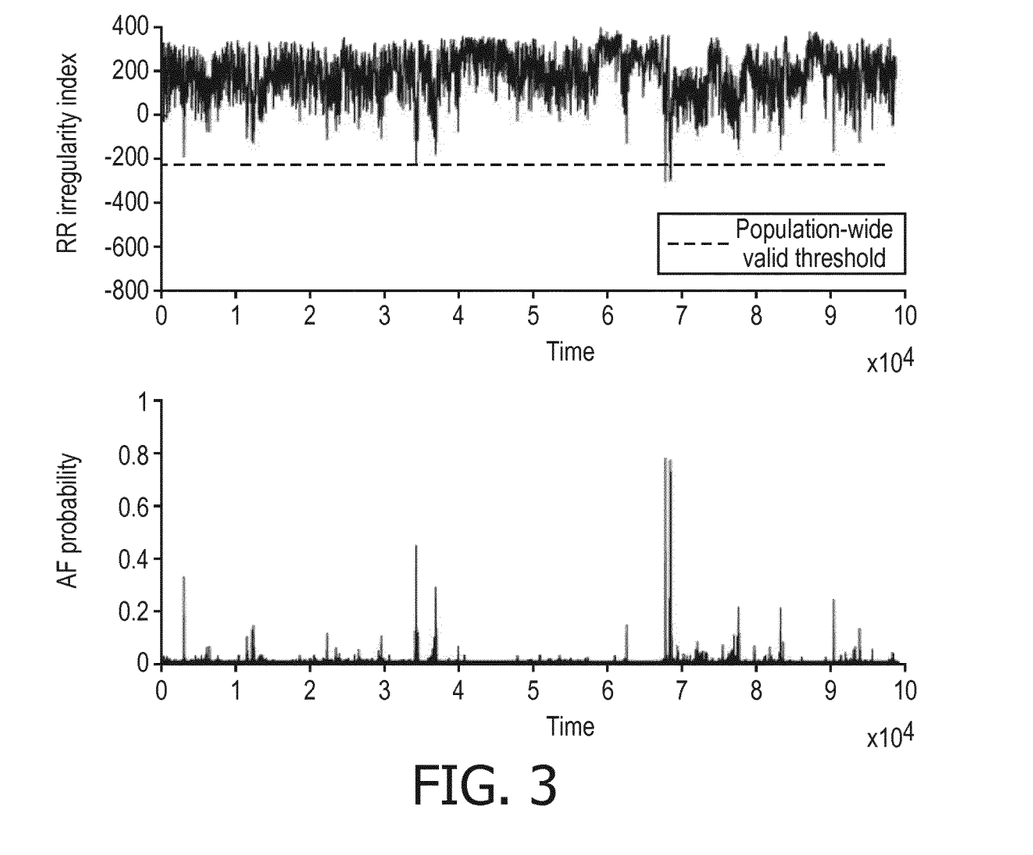
FIG. 3 is a graph of ECG data from a healthy patient, and the corresponding probability of atrial fibrillation, in accordance with an embodiment.

Referring to FIG. 3 is a graph of $RRIR_{IND}$ data obtained from 24 hours of ECG data from a healthy subject, and the corresponding probability of atrial fibrillation obtained using the $RRIR_{IND}$ data. Review of the graph demonstrates that the presence of premature beats in a narrow time period leads to a sharp change in the irregularity index indicating an increase in irregularity. This results in a higher probability of AF and an incorrectly assigned AF event for the patient. Indeed, a high density of premature beats determines a reduction towards negative values of the RR irregularity index, indicating increased irregularity, causing the AF probability to raise and the detection algorithm to erroneously identify AF.

Figure 4:
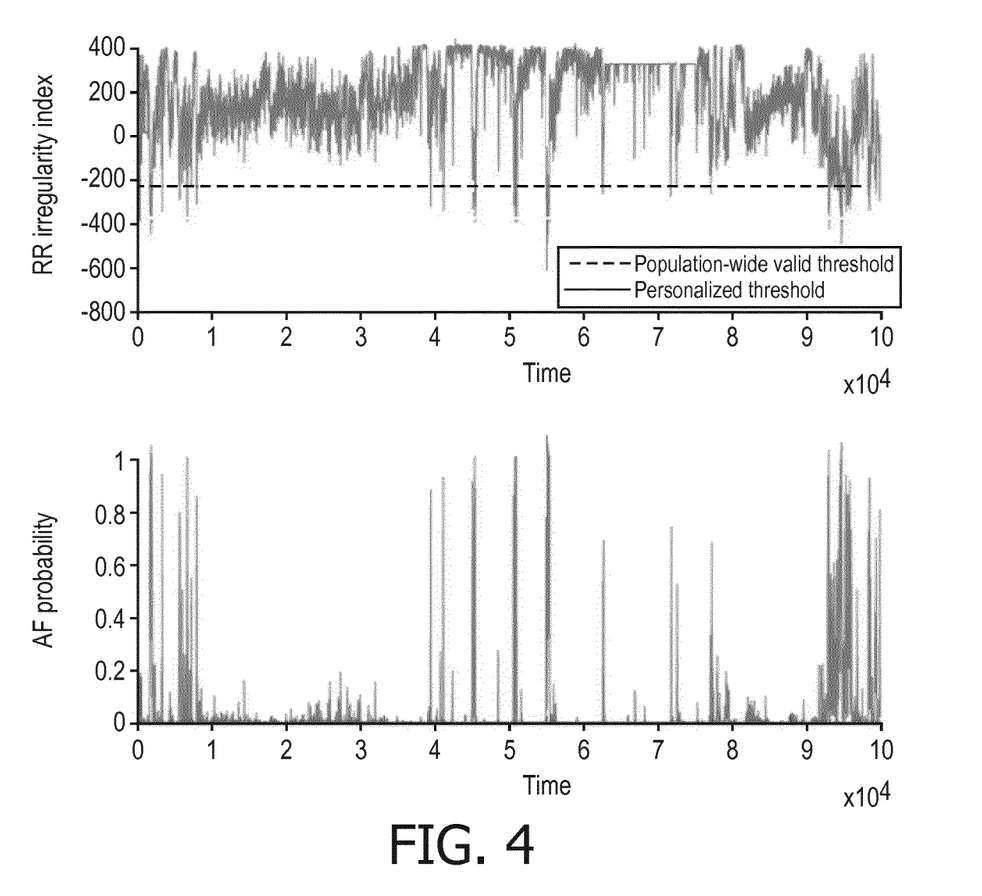
FIG. 4 is a graph of ECG data from a healthy patient, and the corresponding probability of atrial fibrillation, in accordance with an embodiment.

Referring to FIG. 4, in one embodiment, is a graph of $RRIR_{IND}$ data obtained from 24 hours of ECG data from a healthy subject, and the corresponding probability of atrial fibrillation obtained using the $RRIR_{IND}$ data. In contrast to FIG. 3, this graph includes a personalized threshold obtained by integrating ECG and PPG data from a calibration step or stage. This calibration aims at adjusting the detection of AF to the typical RR irregularity observed in a patient due to the characteristic density of premature beats recorded over time.

According to an embodiment, the system may utilize many different integration and calibration methods to generate calibration data and/or one or more personalized thresholds. According to an embodiment, the detection of AF according to an $RRIR_{IND}$ could be assessed with the following equations:

$$normRRIR_{IND} = \frac{Threshold_{AF} - RRIR_{IND}}{\frac{RRIR_{IND}}{4}} \quad \text{Eq. (1)}$$

$$P(AF \mid normRRIR_{IND}) = \frac{1}{1 + e^{-normRRIR_{IND}}} \quad \text{Eq. (1)}$$

If the determined $P(AF|normRRIR_{IND}) > 75\%$ than the system has detected atrial fibrillation. Although the threshold is set to >75%, many other thresholds are possible.

Figure 5:
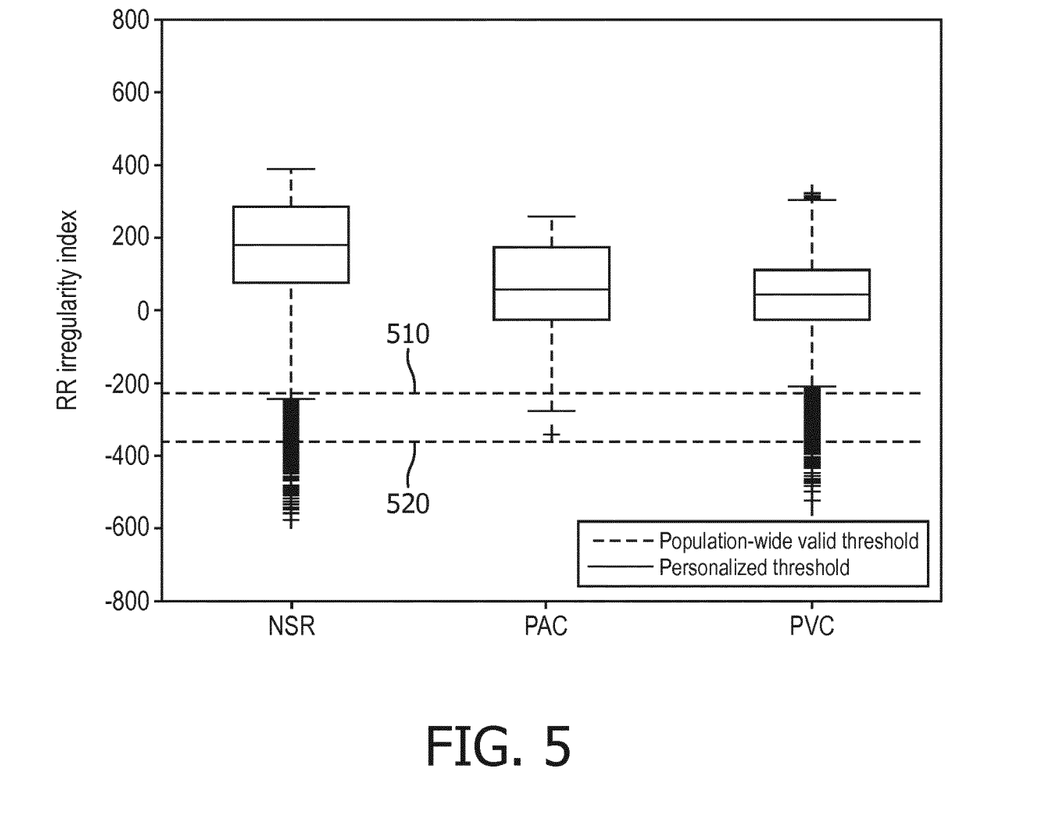
FIG. 5 is a graph of $RR_{irregularity\ index}$ data utilized to determine a personalized arrhythmia threshold, in accordance with an embodiment.

According to an embodiment, the threshold ($Threshold_{AF}$) for $RRIR_{IND}$ can be calibrated in order to reduce AF false positive classification. The calibration aims at adjusting the detection of AF to the typical RR irregularity observed in a patient due to the characteristic density of premature beats recorded over time. Referring to FIG. 5, in one embodiment, is a graph of a method for determining a personalized threshold. The graph includes three different rhythm types—normal sinus rhythm (NSR), premature atrial contraction (PAC), and premature ventricular contraction (PVC)—with an RR irregularity index measured for each. The graph also includes a population-wide AF event threshold 510, and a personalized AF event threshold 520 generated using the integration and calibration data. The AF event threshold can thus be modified to best fit the individually-determined RR irregularity, thereby making the system less prone to adjudicate AF episodes during long series of premature beats.

According to an embodiment, the personalized AF threshold ($Threshold_{AF}$) could be determined from ECG data as the percentile (e.g. 2.5%) of the $RRIR_{IND}$ distribution recorded during a heart event period, including but not limited to NSR, PAC, and/or PVC periods, among others.

According to an embodiment, personalization could also include temporal and/or contextual information in the $Threshold_{AF}$ correction factor. For example, a patient experiencing more premature beats during or after exercise could allow for tailoring the AF detection threshold according to activity participation. As another example, a patient experiencing more premature beats during night hours could allow for tailoring the AF detection threshold according to time of day. Alternatively, patient medication profile and characteristics such as rate and rhythm control medication intake, age, and/or BMI could also be taken into account to modify the AF detection threshold. These and many other factors could be utilized and/or modified to adjust or derive the $Threshold_{AF}$ correction factor.

Figure 6:
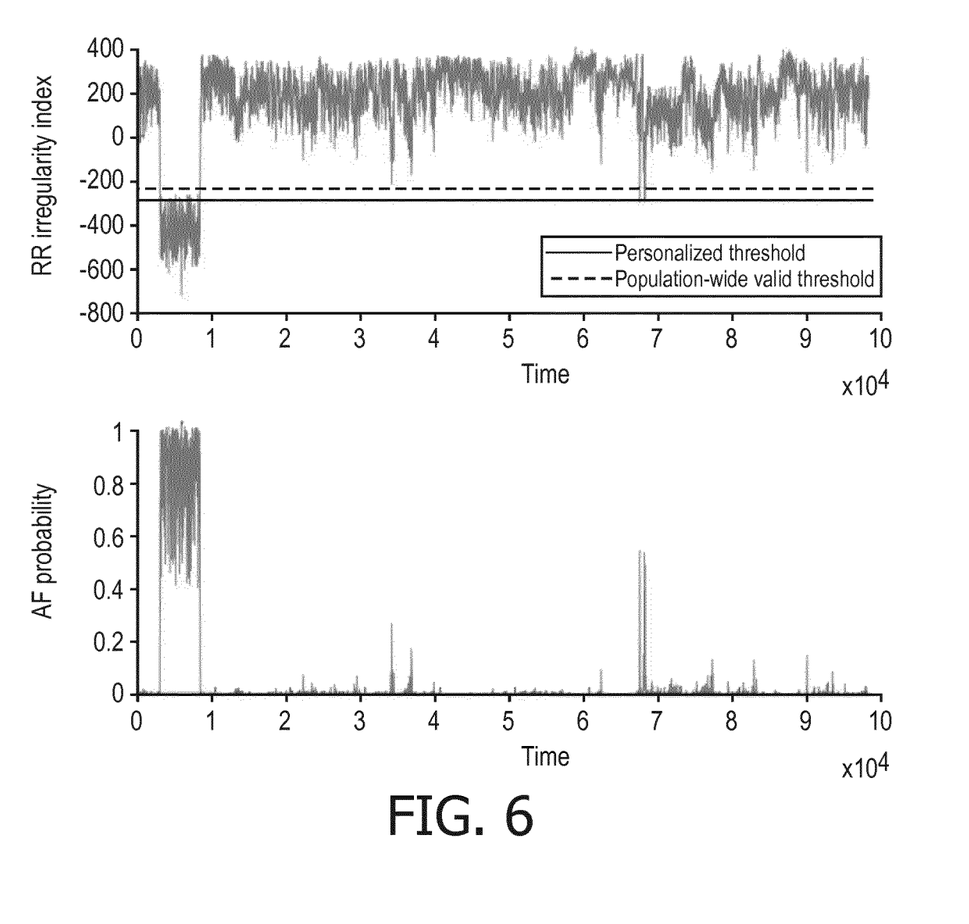
FIG. 6 is a graph of ECG data from a patient, and the corresponding probability of atrial fibrillation, in accordance with an embodiment.

According to an embodiment, the personalized-threshold can be utilized with PPG data to improve AF detection and reduce false positive detection. AF episodes can be accurately detected with the personalized threshold while drastically reducing the false positive AF episodes corresponding to series of premature beats. This allows for reliable and personalized detection of abnormal rhythm irregularities as those due to AF for long term without the need for ECG equipment. Referring to FIG. 6, in one embodiment, is a graph of $RRIR_{IND}$ data obtained from ECG data from an individual, and the corresponding probability of atrial fibrillation obtained using the $RRIR_{IND}$ data. The graph includes a personalized threshold (solid line) and a population-wide threshold (dotted line) obtained by calibration using ECG and PPG data. Compared to previous methods, there is a significant reduction in the number of false positive AF events.

According to an embodiment, the ECG data is not captured simultaneously or synchronously to the PPG data. In this embodiment, the RR irregularity analysis is applied on ECG data only, and the derived irregularity threshold that could characterize periods of normal sinus rhythm with premature beats will then be applied to the PPG data to personalize the computational method used to detect AF events.

At step 150 of the method, the system utilizes the generated calibration data to analyze or calibrate the cardiac activity data obtained by the wearable device during the monitoring phase. This step can occur as the cardiac activity data is collected by the wearable device during the monitoring phase, and/or can occur after the cardiac activity data has been collected. For example, the calibration data can be applied to cardiac activity data collected by the wearable device during any time period, including before or after the calibration data is obtained. As one example, the wearable device or user may store cardiac activity data, and the calibration data could be applied to that stored data. According to an embodiment, the system can utilize the personalized AF event threshold obtained by integrating the ECG and PPG data from the calibration step or stage. This personalized threshold can be applied to the cardiac activity data obtained by the wearable device during the monitoring phase.

At optional step 160 of the method, the system can communicate the resulting data to the individual, a healthcare provider, and/or other intended recipient. For example, the data may be communicated to healthcare professionals including nurses, physicians, and administrators, family members, caregivers, and any other individual capable and/or authorized to receive the data. The data may only be available through a secure link, website, or other portal, and may only be accessible with an access code, QR code, password, biometric parameter, and/or other access mechanism. The data may be automatically provided or uploaded to a caregiver portal, electronic health record database, healthcare professional portal, or other access site. According to another example, the generated report may be automatically delivered to a smartphone, portable computing device, laptop, desktop, or other computer or display via an app or other access.

Figure 7:
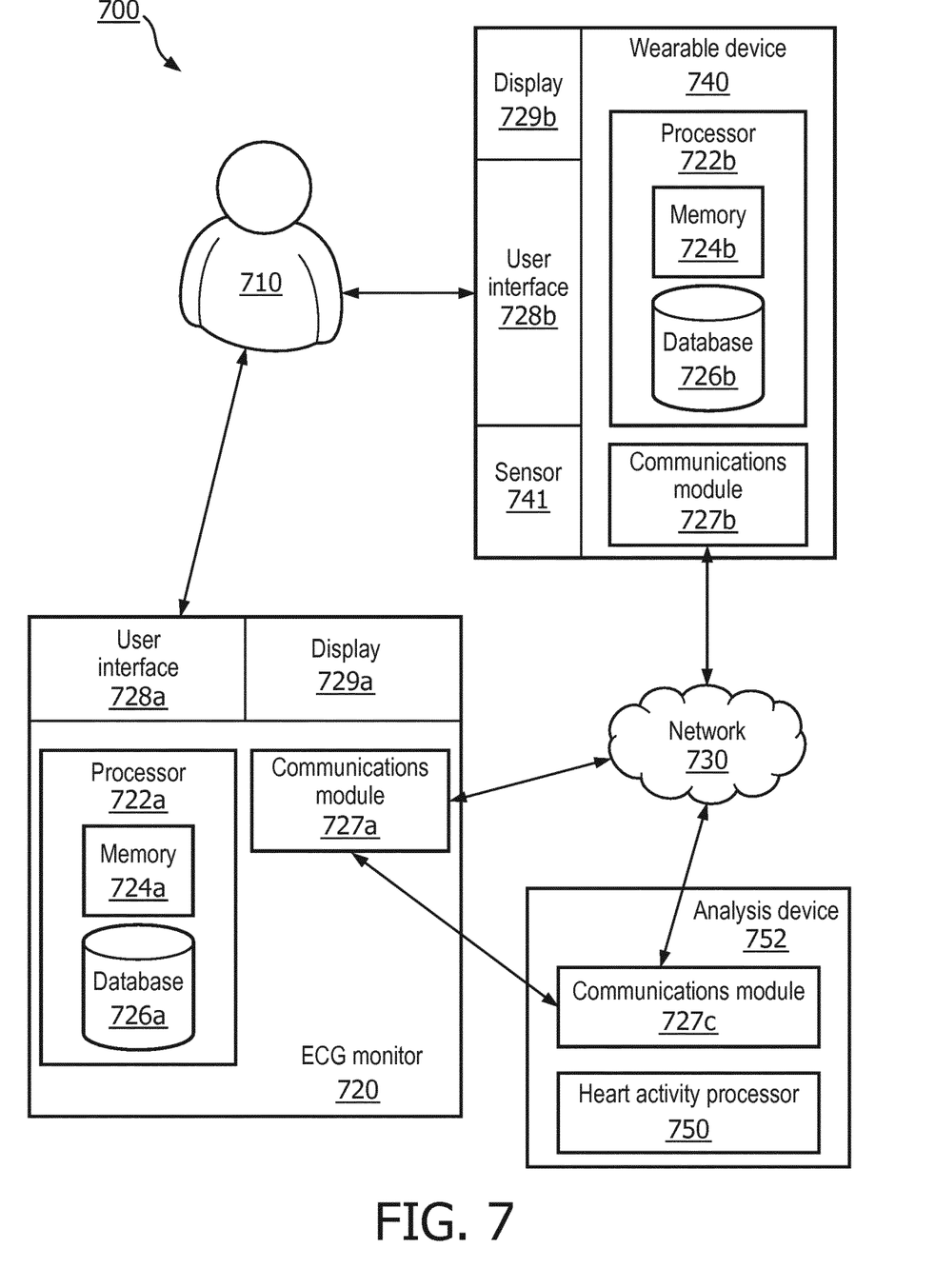
FIG. 7 is a schematic representation of a system for monitoring an individual's cardiac activity, in accordance with an embodiment.

Referring to FIG. 7, in one embodiment, is a cardiac activity monitoring system 700. The cardiac activity monitoring system 700 is configured to implement the method described herein, and can be or include any of the systems described or otherwise envisioned herein. The cardiac activity monitoring system 700 is configured to obtain cardiac activity data about an individual 710, which can be any individual or subject, including an individual with a known medical condition or an individual with no known health issue.

Cardiac activity monitoring system 700 includes an ECG monitor 720. The ECG monitor can be any device configured to or capable of obtaining ECG data about the individual 710, including but not limited to a Holter monitor, among many others. According to an embodiment, ECG monitor 720 can include a processor 722a which is configured or programmed to facilitate the collection and/or communication of ECG data. The processor 722a may be programmed using software to perform various functions discussed herein, and can be utilized in combination with a memory 724a and/or database 726a. The memory and/or database can store data, including one or more commands or software programs for execution by the processor, as well as various types of data. For example, the memory may include a non-transitory computer readable storage medium that includes a set of instructions that are executable by processor, and which cause the system to execute one or more of the steps of the methods described herein. The memory and/or database can also store the ECG data collected from the individual 710.

According to an embodiment, ECG monitor 720 can include an ECG communications module 727a configured to receive and/or send information such as ECG data to a network or other device. The ECG communications module 727a can facilitate wired and/or wireless communication between the ECG monitor and other devices and/or networks, such as a network 730. The ECG communication module 727a may be facilitated through the use of one or more antennas, for example. The ECG communication module can facilitate communication with one or more networks or with other devices, for example, by using wireless methods that are known, including but not limited to Wi-Fi, Bluetooth, 3G, 4G, LTE, and/or ZigBee, among others.

According to an embodiment, ECG monitor 720 can include a user interface 728a to receive input from an individual 710, and/or a healthcare provider or other intended or authorized entity. The user interface may be a button or multiple buttons, a microphone, a key stroke input, a slider, a touchscreen, or any of a variety of other inputs.

According to an embodiment, ECG monitor 720 can include a display 729a which is utilized to provide information such as ECG data, alerts, or other information to the individual 710 and/or to a healthcare provider or other intended or authorized entity. The display may be, for example, an LED-based, LCD-based, or e-paper type display. In other embodiments, the display may be a touch screen display that allows the user to directly interact with the device through physical contact and/or gestures.

Cardiac activity monitoring system 700 also includes a wearable device 740. The wearable device may be a standard wearable device with a sensor, such as an activity monitor, or it may be a smartphone or other sensor intended to obtain sensor data directly from a wearer or user. The wearable device 740 includes a sensor 741 configured to measure, determine, or derive cardiac activity of the user 710. For example, sensor 741 may be a plethysmographic sensor such as a photo-plethysmographic sensor.

According to an embodiment, wearable device 740 can include a processor 722b which is configured or programmed to facilitate the collection and/or communication of ECG data. The processor 722b may be programmed using software to perform various functions discussed herein, and can be utilized in combination with a memory 724b and/or database 726b. The memory and/or database can store data, including one or more commands or software programs for execution by the processor, as well as various types of data. For example, the memory may include a non-transitory computer readable storage medium that includes a set of instructions that are executable by processor, and which cause the system to execute one or more of the steps of the methods described herein. The memory and/or database can also store the ECG data collected from the individual 710.

According to an embodiment, wearable device 740 can include a wearable device communications module 727b configured to receive and/or send information such as sensor data to a network or other device. The wearable device communications module 727b can facilitate wired and/or wireless communication between the wearable device and other devices and/or networks, such as a network 730. The wearable device communication module 727b may be facilitated through the use of one or more antennas, for example. The wearable device communication module can facilitate communication with one or more networks or with other devices, for example, by using wireless methods that are known, including but not limited to Wi-Fi, Bluetooth, 3G, 4G, LTE, and/or ZigBee, among others.

According to an embodiment, wearable device 740 can include a user interface 728b to receive input from an individual 710, and/or a healthcare provider or other intended or authorized entity. The user interface may be a button or multiple buttons, a microphone, a key stroke input, a slider, a touchscreen, or any of a variety of other inputs. According to an embodiment, wearable device 740 can include a display 729b which is utilized to provide information such as sensor data, alerts, or other information to the individual 710 and/or to a healthcare provider or other intended or authorized entity. The display may be, for example, an LED-based, LCD-based, or e-paper type display. In other embodiments, the display may be a touch screen display that allows the user to directly interact with the device through physical contact and/or gestures.

According to an embodiment, cardiac activity monitoring system 700 can include a device 752 which may include a cardiac activity processor 750 and which may be configured to execute one or more steps of the methods described herein. For example, device 752 and/or cardiac activity processor 750 may include a non-transitory computer readable storage medium that includes a set of instructions that are executable by processor, and which cause the system to execute one or more of the steps of the methods described herein. The cardiac activity processor 750 may be located with or remote from one or more of the ECG monitor 720 and the wearable device 740. For example the system may include a wired and/or wireless network 730 that facilitates communication with cardiac activity processor 750 within system 200, and/or between the cardiac activity processor 750 and third-party entities, such as wearable device databases or servers, electronic health record databases, healthcare professionals, or other third parties. Accordingly, the cardiac activity processor 750 may include a communications module 727c configured to receive and/or send information to a network or other device. The communications module 727c can facilitate wired and/or wireless communication between the wearable device and other devices and/or networks, such as a network 730. For example, the cardiac activity processor 750 may be a computer, server, or other processor located at the office of a healthcare professional or in a hospital or other health care location. The cardiac activity processor 750 may receive ECG data from the ECG monitor 720 and sensor data from the wearable device 740 either directly or through network 730. For example, the cardiac activity processor 750 may receive sensor data from the wearable device 740 from a remote server. According to an embodiment, the cardiac activity processor 750 may be one or more of the ECG monitor processor 722*a*, and/or the wearable device processor 722*b*.

According to an embodiment, the cardiac activity processor 750 may perform the calibration steps of the method, including generating one or more personalized thresholds, and analyzing, using the calibration data, sensor data from the wearable device 740 obtaining during the monitoring phase of the method. According to an embodiment, the processor can be configured to store or control the storage of the generated information in local or remote storage. According to yet another embodiment, the cardiac activity processor 750 can be configured to communicate the generated information to the user 710 and/or to a healthcare provider or other intended or authorized entity.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A method for monitoring an individual's cardiac activity, the method comprising the steps of:
    obtaining, during a calibration phase, ECG data for the individual from a ECG monitor;
    obtaining, during the calibration phase, calibration cardiac activity data for the individual from a wearable device comprising a plethysmographic sensor;
    obtaining, during a monitoring phase, monitoring cardiac activity data for the individual from the wearable device comprising the plethysmographic sensor;
    generating calibration data from the ECG data and calibration cardiac activity data obtained during the calibration phase; and
    calibrating, using the calibration data, the monitoring cardiac activity data obtained by the wearable device during the monitoring phase,
    wherein the calibration data comprises a personalized cardiac activity threshold.

2. The method of claim 1, further comprising the step of communicating the calibrated cardiac activity data to at least one of: the individual and another recipient.

3. The method of claim 1, wherein the ECG data, calibration cardiac activity, and monitoring cardiac activity each comprise respective series of R-R irregularity indices.

4. The method of claim 1, wherein obtaining the ECG data comprises:
    receiving R-R interval data from the ECG monitor; and computing a series R-R irregularity indices from the R-R interval data, wherein the ECG data comprises the R-R irregularity indices.

5. The method of claim 1, wherein the calibrating step comprises a comparison of the monitoring cardiac activity data obtained by the wearable device during the monitoring phase to the personalized cardiac activity threshold.

6. The method of claim 1, wherein:
generating the calibration data comprises:
identifying at least one cardiac event from the ECG data, and
generating the personalized threshold based on the cardiac activity data excluding at least one portion of the calibration cardiac activity data corresponding to the at least one cardiac event identified in the ECG data.

7. The method of claim 1, wherein the ECG data is obtained during a first calibration phase, and the cardiac activity data is obtained during a second calibration phase.

8. A system for monitoring an individual's cardiac activity, the system comprising:
an ECG monitor configured to collect ECG data for the individual during a calibration phase;
a wearable device comprising a plethysmographic sensor and configured to collect, via the plethysmographic sensor, cardiac activity data for the individual during the calibration time period and during a monitoring time period; and
a processor configured to: (i) generate calibration data from the ECG data and cardiac activity data obtained during the calibration phase; and (ii) calibrate, using the calibration data, the cardiac activity data obtained by the wearable device during the monitoring phase, wherein the calibration data comprises a personalized cardiac activity threshold.

9. The system of claim 8, wherein the processor is further configured to communicate the calibrated cardiac activity data to at least one of: the individual and another recipient.

10. The system of claim 8, wherein the calibrating step comprises a comparison of the cardiac activity data obtained by the wearable device during the monitoring phase to the personalized cardiac activity threshold.

11. The system of claim 8, wherein the calibration phase and the monitoring phase are not overlapping.

12. The system of claim 8, wherein the ECG data, calibration cardiac activity, and monitoring cardiac activity each comprise respective series of R-R irregularity indices.

13. The system of claim 8, wherein collecting the ECG data comprises:
receiving R-R interval data from the ECG monitor; and
computing a series R-R irregularity indices from the R-R interval data, wherein the ECG data comprises the R-R irregularity indices.

14. The system of claim 8, wherein generating the calibration data comprises:
identifying at least one cardiac event from the ECG data, and
generating the personalized threshold based on the cardiac activity data excluding at least one portion of the calibration cardiac activity data corresponding to the at least one cardiac event identified in the ECG data.

15. A device configured to analyze an individual's cardiac activity, the device comprising a processor configured to execute the steps of:
receiving ECG data obtained by an ECG monitor for an individual during a calibration time period;
receiving cardiac activity data for the individual obtained during the calibration time period by a wearable device comprising a plethysmographic sensor;
generating calibration data from the ECG data and cardiac activity data obtained during the calibration phase; and
calibrating, using the calibration data, the cardiac activity data obtained by the wearable device during the monitoring phase,
wherein the calibration data comprises a personalized cardiac activity threshold.

16. The device of claim 15, wherein the processor is further configured to communicate the calibrated cardiac activity data to at least one of: the individual and another recipient.

17. The device of claim 15, wherein the ECG data, calibration cardiac activity, and monitoring cardiac activity each comprise respective series of R-R irregularity indices.

18. The device of claim 15, wherein receiving the ECG data comprises:
receiving R-R interval data from the ECG monitor; and
computing a series R-R irregularity indices from the R-R interval data, wherein the ECG data comprises the R-R irregularity indices.

19. The device of claim 15, wherein the calibrating step comprises a comparison of the monitoring cardiac activity data obtained by the wearable device during the monitoring phase to the personalized cardiac activity threshold.

20. The device of claim 15, wherein generating the calibration data comprises:
identifying at least one cardiac event from the ECG data, and
generating the personalized threshold based on the cardiac activity data excluding at least one portion of the calibration cardiac activity data corresponding to the at least one cardiac event identified in the ECG data.

* * * * *